US012693290B2

(12) United States Patent
Jordan et al.

(10) Patent No.: US 12,693,290 B2
(45) Date of Patent: Jul. 28, 2026

(54) INTERFERENCE-SUPPRESSED PHARMACOKINETIC IMMUNOASSAY

(71) Applicant: Hoffmann-La Roche Inc., Little Falls, NJ (US)

(72) Inventors: Gregor Jordan, Gröbenzell (DE); Achim Lutz, Iffeldorf (DE); Maria Viert, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1153 days.

(21) Appl. No.: 17/525,187

(22) Filed: Nov. 12, 2021

(65) Prior Publication Data

US 2022/0074928 A1 Mar. 10, 2022

Related U.S. Application Data

(63) Continuation of application No. PCT/EP2020/062965, filed on May 11, 2020.

(30) Foreign Application Priority Data

May 13, 2019 (EP) .................................... 19174196

(51) Int. Cl.
*G01N 33/53* (2006.01)
*G01N 33/68* (2006.01)

(52) U.S. Cl.
CPC ....... *G01N 33/5306* (2013.01); *G01N 33/686* (2013.01)

(58) Field of Classification Search
None
See application file for complete search history.

(56) References Cited

U.S. PATENT DOCUMENTS

| | | | |
|---|---|---|---|
| 4,828,981 A | 5/1989 | Maggio et al. | |
| 2008/0176257 A9* | 7/2008 | Chuntharapai | .... C07K 16/2896 |
| | | | 530/391.1 |

(Continued)

FOREIGN PATENT DOCUMENTS

| | | |
|---|---|---|
| JP | 2013519375 A | 5/2013 |
| JP | 2017223710 A | 12/2017 |
| JP | 2018508188 A | 3/2018 |

OTHER PUBLICATIONS

Smith et al. (Detection of antibodies against therapeutic proteins in the presence of residual therapeutic protein using a solid-phase extraction with acid dissociation (SPEAD) sample treatment prior to ELISA, Regulatory Toxicology and Pharmacology, vol. 49, issue 3, 2007, IDS filed Mar. 9, 2026) (Year: 2007).*

(Continued)

*Primary Examiner* — Bao-Thuy L Nguyen
*Assistant Examiner* — Chau N.B. Tran
(74) *Attorney, Agent, or Firm* — Hoffmann-La Roche Inc.

(57) ABSTRACT

Herein is reported a method for the determination of a bispecific antibody in a serum-containing sample comprising the steps of first incubating a solid phase to which a capture antibody specifically binding to the bispecific antibody has been immobilized with the sample to form an immobilized capture antibody-bispecific antibody-complex, thereafter incubating the solid phase with a replacement antibody that competes with the capture antibody for binding to the bispecific antibody and thereby forming a solution comprising a replacement antibody-bispecific antibody-complex, and determining in the solution the replacement antibody-bispecific antibody-complex.

9 Claims, 6 Drawing Sheets

| solid phase:<br>SA-MTP | capture reagent:<br>biotinylated<br>anti-idiotypic antibody<br>against binding specificity 1 | bispecific antibody | detection reagent:<br>digoxygenylated<br>anti-idiotypic antibody<br>against binding specificity 2 | anti-digoxygenin antibody-<br>enzyme conjugate |

(56)  References Cited

U.S. PATENT DOCUMENTS

| | | | |
|---|---|---|---|
| 2010/0261292 A1* | 10/2010 | Glezer | G01N 33/54313 205/775 |
| 2014/0342382 A1 | 11/2014 | Stubenrauch et al. | |
| 2015/0198608 A1* | 7/2015 | Stubenrauch | G01N 33/686 435/7.92 |
| 2016/0108126 A1 | 4/2016 | Deckert et al. | |
| 2016/0223530 A1 | 8/2016 | Marshall et al. | |
| 2017/0355767 A1 | 12/2017 | Engelberts et al. | |

OTHER PUBLICATIONS

Bacac, M., et al., "CD20-TCB with Obinutuzumab Pretreatment as Next-Generation Treatment of Hematologic Malignancies" Clin Cancer Res 24(19):4785-4797 (Oct. 1, 2018).

De Zwart, M., et al., "Co-medication and interference testing in bioanalysis: a European Bioanalysis Forum recommendation" Bioanalysis 8(19):2065-2070 (Oct. 1, 2016).

"International Preliminary Report on Patentability—PCT/EP2020/062965" (Report Issuance Date: Nov. 16, 2021; Chapter I),:pp. 1-7 (Nov. 25, 2021).

"International Search Report—PCT/EP2020/062965" (w/Written Opinion),:pp. 1-12 (Jul. 14, 2020).

Sun, L., et al., "Anti-CD20/CD3 T cell-dependent bispecific antibody for the treatment of B cell malignancies" Sci Trans Med 7(287):287ra70 (1-10) (May 13, 2015).

Tate, J., et al., "Interferences in Immunoassay" Clin Biochemist Rev 25(2):105-120 (May 1, 2004).

Smith, H., et al., "Detection of antibodies against therapeutic proteins in the presence of residual therapeutic protein using a solid-phase extraction with acid dissociation (SPEAD) sample treatment prior to Elisa" Regul Toxicol Pharmacol 49(3):230-237 (Dec. 1, 2007).

* cited by examiner anti-digoxygenin antibody-
enzyme conjugate detection reagent:
digoxygenylated
anti-idiotypic antibody
against binding specificity 2 bispecific antibody capture reagent:
biotinylated
anti-idiotypic antibody
against binding specificity1 solid phase:
SA-MTP

ABTS anti-digoxygenin antibody-enzyme conjugate detection reagent:
digoxygenylated
anti-idiotypic antibody
against binding specificity 2 monospecific antibody
comprising binding site of
bispecific antibody solid phase:
SA-MTP Serum concentration [ng/mL]

INTERFERENCE-SUPPRESSED PHARMACOKINETIC IMMUNOASSAY

CROSS REFERENCE TO RELATED APPLICATIONS

This application is a continuation of and claims the right of priority under 35 U.S.C. § 120 to International Application No. PCT/EP2020/062965, filed May 11, 2020, which claims the benefit of priority to European Patent Application No. 19174196.6, filed May 13, 2019, both of which are commonly owned with the present application, and the entire contents of both of which are hereby expressly incorporated by reference in their entirety as though fully set forth herein.

The current invention is in the field of immunoassays, more specifically in the field of pharmacokinetic immunoassays. Herein is reported amongst other things an interference-suppressed immunoassay for the detection of a bispecific antibody in a serum-containing sample in the presence of an interfering monospecific antibody.

BACKGROUND

For the analysis of therapeutic monoclonal antibodies (tmAbs) in samples of in vitro or in vivo origin a respective assay is necessary, especially in early stages of tmAb development. This requires the provision of specific binding reagents, such as anti-idiotypic antibodies for the determination of the tmAb.

Especially for full pharmacokinetic evaluation of a tmAb knowledge of soluble tmAb concentrations in plasma/serum samples after dosing under treatment-like conditions is important.

Lee, J. W., et al. (AAPS J. 13 (2011) 99-110) report that the predominant driver of bioanalysis in supporting drug development is the intended use of the data. Reliable methodologies for measurements of mAb and its antigen ligand (L) in circulation are crucial for the assessment of exposure-response relationships in support of efficacy and safety evaluations, and dose selection.

De Zwart et al. (Bioanal. 8 (2016) 2065-2070) reported in a white paper about the interference testing of co-medication in bioanalytical method validation. Survey data used by de Zwart et al. on past experience led them to the conclusion that there were no instances where co-medication interfered with the LC-MS/MS assays of the investigational drug for both scheduled and unscheduled co-medication (data from 389 observations), whereas for LBA-based assays, the survey data identified only one out of 36 assays where interference was reported.

Ligand-binding assays (LBA) are widely used for the analysis of protein biotherapeutics and antigen ligands (L) to support pharmacokinetics/pharmacodynamics (PK/PD) and safety assessments.

SUMMARY OF THE INVENTION

Herein is reported an immunoassay for the determination of the presence or the amount of an at least bispecific (therapeutic) antibody in a serum containing sample. In more detail, the assay is a two-step assay comprising a replacement step for reducing interference from a monospecific (therapeutic) antibody also present in the sample. Thus, the interference originating from the presence of a second antibody comprising one binding site of the at least bispecific antibody in the immunoassay can be reduced. In the immunoassay according to the invention for the first time such an intermediate replacement step has been employed for the reduction of immunoassay-interference.

One aspect according to the invention is a method for the determination of a multispecific therapeutic, preferably bispecific, antibody in a serum-containing sample comprising the following steps:

a) incubating a solid phase to which a capture antibody that is specifically binding to the therapeutic antibody has been immobilized with the sample to form an immobilized capture antibody-therapeutic antibody-complex, b) optionally washing the solid phase whereby the capture antibody-therapeutic antibody-complex remains bound to the solid phase, c) incubating the solid phase with a replacement antibody that sterically interferes with the binding of the capture antibody to the therapeutic antibody, or that competes with the capture antibody for binding to the therapeutic antibody, or that binds to the same epitope as the capture antibody on the therapeutic antibody and thereby detaching the therapeutic antibody from the solid phase and forming a solution comprising a replacement antibody-therapeutic antibody-complex, d) determining in the solution obtained in step c) the replacement antibody-therapeutic antibody-complex and thereby determining the therapeutic antibody in a serum-containing sample.

A further aspect according to the invention is a method for enriching a therapeutic antibody, preferably a multispecific, most preferably a bispecific antibody, from a serum-containing sample comprising the following steps:

a) incubating a solid phase to which a capture antibody that is specifically binding to the therapeutic antibody has been immobilized with the sample to form an immobilized capture antibody-therapeutic antibody-complex, b) optionally washing the solid phase whereby the capture antibody-therapeutic antibody-complex remains bound to the solid phase, c) incubating the solid phase with a replacement antibody that competes with the capture antibody for binding to the therapeutic antibody and thereby detaching the therapeutic antibody from the solid phase and forming a solution comprising a replacement antibody-therapeutic antibody-complex, thereby enriching the therapeutic antibody from a serum-containing sample.

In one embodiment of all aspects and embodiments the replacement antibody is an antibody with the same specificity as the capture antibody and with (slightly) higher affinity. In one embodiment the replacement antibody has a $K_D$-value (as measure for the binding affinity) for binding to the therapeutic antibody that is one order of magnitude lower as the $K_D$-value of the capture antibody.

In one embodiment of all aspects and embodiments the capture antibody is biotinylated, the solid phase is conjugated to streptavidin and the immobilization of the capture antibody is by the interaction of biotin of the antibody and streptavidin of the solid phase.

In one embodiment of all aspects and embodiments the detecting of the replacement antibody-therapeutic antibody-complex is in an immunoassay. In one embodiment the immunoassay is a bridging immunoassay, preferably a bridging ELISA.

In one embodiment of all aspects and embodiments the replacement antibody is labelled and the determining of the replacement antibody-therapeutic antibody-complex is by detecting said label. In one embodiment the replacement antibody is conjugated to digoxygenin and the detecting is by an anti-digoxygenin antibody.

In one embodiment of all aspects and embodiments the therapeutic antibody comprises a first binding site specifically binding to a first antigen and a second binding site specifically binding to a second antigen. In one embodiment the therapeutic antibody is a bispecific, trivalent antibody with one binding site specifically binding to the first antigen and two binding sites specifically binding to the second antigen.

In one embodiment of all aspects and embodiments the capture antibody or the replacement antibody or both are an anti-idiotypic antibody. In one embodiment the capture antibody or the replacement antibody or both are an anti-idiotypic antibody specifically binding to the first binding site of the therapeutic antibody.

In one preferred embodiment of all aspects and embodiments the capture antibody is an anti-idiotypic antibody directed/specifically binding to the first binding site of the bispecific therapeutic antibody.

In one preferred embodiment of all aspects and embodiments the replacement antibody is an anti-idiotypic antibody directed/specifically binding to the first binding site of the bispecific therapeutic antibody.

In one preferred embodiment of all aspects and embodiments the capture and the replacement antibody are different anti-idiotypic antibodies directed/specifically binding to the first binding site of the bispecific therapeutic antibody.

In one embodiment of all aspects and embodiments the capture of the replacement antibody-therapeutic antibody soluble complex is via an immobilized anti-idiotypic antibody specifically binding to the second binding specificity of the therapeutic antibody and detection is via a detectable label conjugated to the replacement antibody.

In one embodiment of all aspects and embodiments step d) is incubating the solution obtained in step c) with a second solid phase to which a second capture molecule, preferably a second capture antibody (that is different from the first capture antibody), specifically binding to the therapeutic antibody (e.g. the second antigen or an anti-idiotypic antibody specifically binding to the second binding site of the therapeutic antibody or an antibody specifically binding to the constant region/constant domains of a human antibody) has been immobilized with the solution comprising the replacement antibody-therapeutic antibody-complex to form an immobilized second capture molecule-therapeutic antibody-replacement antibody complex and the determining is by determining said immobilized second capture molecule-therapeutic antibody-replacement antibody complex. In one embodiment the second capture molecule does not compete with the replacement antibody for binding to the therapeutic antibody.

In one embodiment of all aspects and embodiments the replacement antibody is an antibody with the same binding specificity (same epitope) as the capture antibody or the capture antibody itself.

In one embodiment of all aspects and embodiments the solid phase in step c) is incubated with the replacement antibody at a concentration of about 6.67 nM or more.

In one embodiment of all aspects and embodiments the serum-containing sample comprises the therapeutic antibody, which is a multispecific antibody, and a monospecific antibody comprising one binding site of the therapeutic antibody and the method is a method with reduced interference by the monospecific antibody in the determination of presence or amount of the therapeutic antibody. In one embodiment the sample is obtained from an individual to which the monospecific antibody has been applied prior to the application of the therapeutic antibody.

In one embodiment of all aspects and embodiments the therapeutic antibody is a bispecific antibody or a trispecific antibody or a tetraspecific antibody. In one preferred embodiment the therapeutic antibody is a bispecific (therapeutic) antibody. In one embodiment the bispecific (therapeutic) antibody is a TCB.

In one embodiment of all aspects and embodiments the bispecific (therapeutic) antibody comprises a first and a second Fab fragment, wherein each binding site of the first and the second Fab fragment specifically bind to the second antigen, a third Fab fragment, wherein the binding site of the third Fab fragment specifically binds to the first antigen, and wherein the third Fab fragment comprises a domain crossover such that the variable light chain domain (VL) and the variable heavy chain domain (VH) are replaced by each other, and an Fc-region comprising a first Fc-region polypeptide and a second Fc-region polypeptide, wherein the first and the second Fab fragment each comprise a heavy chain fragment and a full length light chain, wherein the C-terminus of the heavy chain fragment of the first Fab fragment is fused to the N-terminus of the first Fc-region polypeptide, wherein the C-terminus of the heavy chain fragment of the second Fab fragment is fused to the N-terminus of the variable light chain domain of the third Fab fragment and the C-terminus of the heavy chain constant domain 1 of the third Fab fragment is fused to the N-terminus of the second Fc-region polypeptide.

In one embodiment of all aspects and embodiments the bispecific (therapeutic) antibody is an anti-CD3/CD20 bispecific antibody. In one embodiment the anti-CD3/CD20 bispecific antibody is a TCB with CD20 being the second antigen. In one embodiment the bispecific anti-CD3/CD20 antibody is RG6026.

In one embodiment of all aspects and embodiments the monospecific antibody is an anti-CD20 antibody. In one embodiment the anti-CD20 antibody is obinutuzumab.

In one embodiment of all aspects and embodiments the method is for determining target-binding-competent multispecific (bispecific) antibody.

In one embodiment of all aspects and embodiments the method is for determining target-binding-competence of two (both) binding sites of a multispecific (bispecific) antibody.

In one embodiment of all aspects and embodiments the sample comprises at least 10% (v/v) serum. In one embodiment the sample comprises about 50% (v/v) serum.

In one embodiment of all aspects and embodiments the solid phase is the well of a multi-well-plate (MTP). In one embodiment the MTP is a 96-well-multi well plate. In one embodiment the well of the multi-well-plate has a total volume of 320-360 µL. In one embodiment the well of the multi-well-plate has a working volume of 100-200 µL.

In one embodiment of all aspects and embodiments the replacement antibody has a concentration of 0.75 µg/mL or more. In one preferred embodiment the replacement antibody has a concentration of about 1 µg/mL or more.

In one embodiment of all aspects and embodiments more than 100 µL of a solution comprising the replacement antibody is added to the solid phase. In one embodiment more than 115 µl of a solution comprising the replacement antibody is added to the solid phase. In one preferred embodiment 135 μL or more of a solution comprising the replacement antibody is added.

In one embodiment of all aspects and embodiments the incubating with the replacement antibody is for 1 hour or more. In one embodiment the incubating with the replacement antibody is for 1.5 hours or more. In one embodiment the incubating with the replacement antibody is for 2 hours or more. In one preferred embodiment the incubating with the replacement antibody is for about 2.5 hours or more.

In one embodiment of all aspects and embodiments more than 100 μL of a solution comprising the replacement antibody at a concentration of about 0.75 μg/mL or more is added to the solid phase and incubated for about 1.5 hours or more.

DETAILED DESCRIPTION OF EMBODIMENTS OF THE INVENTION

Herein is reported an immunoassay for the determination of an at least bispecific antibody in a serum containing sample using a replacement step. Thereby the interference originating from the presence of a second antibody comprising one binding site of the at least bispecific antibody in the immunoassay can be reduced. In the immunoassay according to the invention for the first time such an intermediate replacement step has been employed for the reduction of immunoassay-interference.

The current invention is based at least in part on the finding that the detection of a multispecific, therapeutic antibody in a serum containing sample in an immunoassays can be improved (reducing or even eliminating non-specific interference originating from the presence of a second antibody comprising one binding site of the multispecific antibody) by inserting an additional replacement step after the capture of the multispecific, therapeutic antibody on a solid phase. In the replacement step the capture antibody-therapeutic antibody-complex is incubated with a replacement antibody (sterically) competing with the capture antibody for binding to the therapeutic antibody, e.g. by binding to the same epitope or a closely related epitope on the therapeutic antibody. The displacement of the capture antibody by the replacement antibody effects the desorption of the captured therapeutic antibody from the solid phase to form an intermediate soluble complex. This intermediate complex can then be detected with reduced or even eliminated interference by the antibody comprising one binding site of the therapeutic antibody in a subsequent step.

Definitions

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The terms "therapeutic (monoclonal) antibody" and "drug" are used interchangeably herein. These terms are used in the broadest sense and encompasses various antibody structures, including but not limited to monoclonal antibodies, polyclonal antibodies, and antibody fragments so long as they exhibit the desired antigen-binding activity.

An antibody in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The constant domains of an antibody heavy chain comprise the CH1-domain, the CH2-domain and the CH3-domain, whereas the light chain comprises only one constant domain, CL, which can be of the kappa isotype or the lambda isotype.

The variable domain of an immunoglobulin's light or heavy chain in turn comprises different segments, i.e. four framework regions (FR) and three hypervariable regions (HVR).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al.

The term "valent" as used within the current application denotes the presence of a specified number of binding sites in a (antibody) molecule. As such, the terms "bivalent", "tetravalent", and "hexavalent" denote the presence of two binding sites, four binding sites, and six binding sites, respectively, in a (antibody) molecule. The bispecific antibodies as reported herein are in one preferred embodiment "bivalent".

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "binding (to an antigen)" denotes the binding of an antibody to its antigen in an in vitro assay, in one embodiment in a binding assay in which the antibody is bound to a surface and binding of the antigen to the antibody is measured by Surface Plasmon Resonance (SPR). Binding means the measurement of the binding capacity of e.g. the antibody for target A or target B, or for a capture molecule e.g. anti-human-Fab-capture for the antibody.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "sample" includes, but is not limited to, any quantity of a substance from a living thing or formerly living thing. Such living things include, but are not limited to, humans, mice, monkeys, rats, rabbits, and other animals. In one embodiment the sample is obtained from a monkey, especially a cynomolgus monkey, or a rabbit, or a mouse, or rat, or a human. In one preferred embodiment the sample is a human sample. Such substances include, but are not limited to, in one embodiment whole blood, plasma or serum from an individual, which are the most widely used sources of sample in clinical routine.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

The term "immunoassay" denotes any technique that utilizes specifically binding molecules, such as antibodies, to capture and/or detect a specific target for qualitative or quantitative analysis. In general, an immunoassay is characterized by the following steps: 1) immobilization or capture of the analyte and 2) detection and measuring the analyte. The analyte can be captured, i.e. bound, on any solid surface, such as e.g. a membrane, plastic plate, or some other solid surface.

Multispecific Antibodies

In certain embodiments, the drug is a bispecific antibody. In one embodiment the drug is a bispecific, trivalent antibody. In one preferred embodiment the drug is a monoclonal, bispecific, trivalent antibody.

In certain embodiments, the drug is a multispecific antibody, e.g. a bispecific antibody. Multispecific antibodies are monoclonal antibodies that have binding specificities for at least two different antigens. In certain embodiments, one of the binding specificities is for a first antigen and the other is for a different second antigen. Bispecific antibodies can be prepared as full length antibodies or antibody fragments. In one embodiment the antibody is a bispecific antibody, which specifically binds to a first and a second antigen. In one embodiment the bispecific antibody has i) a first binding specificity that specifically binds to a first antigen, and ii) a second binding specificity that specifically binds to a second antigen. In one embodiment the antibody is a bispecific, trivalent antibody. In one preferred embodiment the antibody is a monoclonal, bispecific, trivalent antibody.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (scFv) dimers (see, e.g., Gruber, M., et al., J. Immunol. 152 (1994) 5368-5374); and preparing trispecific antibodies as described, e.g., in Tutt, A., et al., J. Immunol. 147 (1991) 60-69).

Multispecific antibodies are described in WO 2009/080251, WO 2009/080252, WO 2009/080253, WO 2009/080254, WO 2010/112193, WO 2010/115589, WO 2010/136172, WO 2010/145792, or WO 2010/145793.

Different bispecific antibody formats are known.

Exemplary bispecific antibody formats for which the methods as reported herein can be used are the domain exchange format: a multispecific IgG antibody comprising a first Fab fragment and a second Fab fragment, wherein in the first Fab fragment
a) only the CH1 and CL domains are replaced by each other (i.e. the light chain of the first Fab fragment comprises a VL and a CH1 domain and the heavy chain of the first Fab fragment comprises a VH and a CL domain);
b) only the VH and VL domains are replaced by each other (i.e. the light chain of the first Fab fragment comprises a VH and a CL domain and the heavy chain of the first Fab fragment comprises a VL and a CH1 domain); or
c) the CH1 and CL domains are replaced by each other and the VH and VL domains are replaced by each other (i.e. the light chain of the first Fab fragment comprises a VH and a CH1 domain and the heavy chain of the first Fab fragment comprises a VL and a CL domain); and wherein the second Fab fragment comprises a light chain comprising a VL and a CL domain, and a heavy chain comprising a VH and a CH1 domain;

the domain exchange antibody may comprises a first heavy chain including a CH3 domain and a second heavy chain including a CH3 domain, wherein both CH3 domains are engineered in a complementary manner by respective amino acid substitutions, in order to support heterodimerization of the first heavy chain and the modified second heavy chain, e.g. as disclosed in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, or WO 2013/096291 (incorporated herein by reference);

the one-armed single chain format (=one-armed single chain antibody): antibody comprising a first binding site that specifically binds to a first antigen and a second binding site that specifically binds to a second antigen, whereby the individual chains are as follows light chain (variable light chain domain+light chain kappa constant domain)

combined light/heavy chain (variable light chain domain+light chain constant domain+peptidic linker+variable heavy chain domain+CH1+Hinge+CH2+CH3 with knob mutation)

heavy chain (variable heavy chain domain+CH1+Hinge+CH2+CH3 with hole mutation);

the two-armed single chain format (=two-armed single chain antibody): antibody comprising a first binding site that specifically binds to a first antigen and a second binding site that specifically binds to a second antigen, whereby the individual chains are as follows combined light/heavy chain 1 (variable light chain domain+light chain constant domain+peptidic linker+variable heavy chain domain+CH1+Hinge+CH2+CH3 with hole mutation)

combined light/heavy chain 2 (variable light chain domain+light chain constant domain+peptidic linker+variable heavy chain domain+CH1+Hinge+CH2+CH3 with knob mutation);

the common light chain bispecific format (=common light chain bispecific antibody): antibody comprising a first binding site that specifically binds to a first antigen and a second binding site that specifically binds to a second antigen, whereby the individual chains are as follows light chain (variable light chain domain+light chain constant domain)

heavy chain 1 (variable heavy chain domain+CH1+Hinge+CH2+CH3 with hole mutation)

heavy chain 2 (variable heavy chain domain+CH1+Hinge+CH2+CH3 with knob mutation);

the dual targeting Fab: Fab comprising two (non-overlapping) paratopes in a complementary pair of a VH and a VL domain, wherein the first paratope comprises (consists of) amino acid residues from CDR1 and CDR3 of the VL domain and CDR2 of the VH domain, and the second paratope comprises (consists of) residues from CDR1 and CDR3 of the VH domain and CDR2 of the VL domain; the term "non-overlapping" in this context indicates that an amino acid residue that is comprised within the first paratope of the DutaFab is not comprised in the second paratope, and an amino acid that is comprised within the second paratope of the DutaFab is not comprised in the first paratope the T-cell bispecific format (TCB): a bispecific antibody comprising a first and a second Fab fragment, wherein each binding site of the first and the second Fab fragment specifically bind to a second antigen, a third Fab fragment, wherein the binding site of the third Fab fragment specifically binds to a first antigen, and wherein the third Fab fragment comprises a domain crossover such that the variable light chain domain (VL) and the variable heavy chain domain (VH) are replaced by each other, and an Fc-region comprising a first Fc-region polypeptide and a second Fc-region polypeptide, wherein the first and the second Fab fragment each comprise a heavy chain fragment and a full length light chain, wherein the C-terminus of the heavy chain fragment of the first Fab fragment is fused to the N-terminus of the first Fc-region polypeptide, wherein the C-terminus of the heavy chain fragment of the second Fab fragment is fused to the N-terminus of the variable light chain domain of the third Fab fragment and the C-terminus of the heavy chain constant domain 1 of the third Fab fragment is fused to the N-terminus of the second Fc-region polypeptide.

In one embodiment the bispecific antibody is a domain exchanged antibody.

In one embodiment the bispecific antibody is a one-armed single chain antibody.

In one embodiment the bispecific antibody is a two-armed single chain antibody.

In one embodiment the bispecific antibody is a common light chain bispecific antibody.

In one embodiment the bispecific antibody is a dual targeting Fab.

In one embodiment the bispecific antibody is a T-cell bispecific antibody.

Multivalent, multispecific antibodies specifically bind to different targets, most likely with different affinities and complex stabilities for each target. Only a fully active multivalent, multispecific antibody can bind to all targets and shows the full biological activity in a corresponding assay.

The term "CD20-TCB" as used herein denotes a CD20-targeting TCB (CD20-TCB; RG6026; anti-CD3/CD20 antibody in TCB format), which has a long half-life and high potency enabled by high-avidity bivalent binding to CD20 and head-to-tail orientation of B- and T-cell-binding domains in a previously characterized 2:1 TCB molecular format (see e.g. Bacac, M., et al., Clin. Cancer Res. 22 (2016) 3286-3297; Bacac, M., et al., Oncoimmunology 5 (2016) e1203498).

Immunoassays

The principles of different immunoassays are described in the art. For example, Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Monoclonal antibodies and their constant domains contain a number of reactive amino acid side chains for conjugating to a member of a binding pair, such as a polypeptide/protein, a polymer (e.g. PEG, cellulose or polystyrol), or an enzyme. Chemical reactive groups of amino acids are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pages 50-100.

One of the most common reactive groups of antibodies is the aliphatic F-amine of the amino acid lysine. In general, nearly all antibodies contain abundant lysine. Lysine amines are reasonably good nucleophiles above pH 8.0 (pKa=9.18) and therefore react easily and cleanly with a variety of reagents to form stable bonds. Amine-reactive reagents react primarily with lysins and the α-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiff's base). A Schiff's base can be selectively reduced with mild or strong reducing agents (such as sodium borohydride or sodium cyanoborohydride) to derive a stable alkyl amine bond. Other reagents that have been used to modify amines are acid anhydrides. For example, diethyl-enetriaminepentaacetic anhydride (DTPA) is a bifunctional chelating agent that contains two amine-reactive anhydride groups. It can react with N-terminal and ε-amine groups of amino acids to form amide linkages. The anhydride rings open to create multivalent, metal-chelating arms able to bind tightly to metals in a coordination complex.

Another common reactive group in antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiothreitol (DTT) is required to generate the reactive free thiol. Thiol-reactive reagents are those that will couple to thiol groups on polypeptides, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succin-imidyl (acetylthio) acetate (SATA), and sulfosuccinimidyl 6-[3-(2-pyridyldithio) propionamido]hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodo-acetamides. Maleimides react rapidly at slight acidic to neutral pH.

Another common reactive group in antibodies are car-boxylic acids. Antibodies contain carboxylic acid groups at the C-terminal position and within the side chains of aspartic acid and glutamic acid. The relatively low reactivity of carboxylic acids in water usually makes it difficult to use these groups to selectively modify polypeptides and anti-bodies. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic F-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is pre-dominantly found on the crystallizable fragment region (Fc-region) of an antibody, conjugation can be achieved through site-directed modification of the carbohydrate away from the antigen-binding site. A Schiff's base intermediate is formed, which can be reduced to an alkyl amine through the reduction of the intermediate with sodium cyanoborohy-dride (mild and selective) or sodium borohydride (strong) water-soluble reducing agents.

The conjugation of a tracer and/or capture and/or detec-tion antibody to its conjugation partner can be performed by different methods, such as chemical binding, or binding via a binding pair. The term "conjugation partner" as used herein denotes e.g. solid supports, polypeptides, detectable labels, members of specific binding pairs. In one embodi-ment the conjugation of the capture and/or tracer and/or detection antibody to its conjugation partner is performed by chemically binding via N-terminal and/or ε-amino groups (lysine), ε-amino groups of different lysines, carboxy-, sulf-hydryl-, hydroxyl-, and/or phenolic functional groups of the amino acid backbone of the antibody, and/or sugar alcohol groups of the carbohydrate structure of the antibody. In one embodiment the capture antibody is conjugated to its con-jugation partner via a binding pair. In one preferred embodi-ment the capture antibody is conjugated to biotin and immobilization to a solid support is performed via solid support immobilized avidin or streptavidin. In one embodi-ment the capture antibody is conjugated to its conjugation partner via a binding pair. In one preferred embodiment the tracer antibody is conjugated to digoxigenin by a covalent bond as detectable label.

Chromogens (fluorescent or luminescent groups and dyes), enzymes, NMR-active groups or metal particles, haptens, e.g. digoxigenin, are examples of "detectable labels". The detectable label can also be a photoactivatable crosslinking group, e.g. an azido or an azirine group. Metal chelates which can be detected by electrochemilumines-cense are also preferred signal-emitting groups, with par-ticular preference being given to ruthenium chelates, e.g. a ruthenium (bispyridyl)32+chelate. Suitable ruthenium label-ing groups are described, for example, in EP 0 580 979, WO 90/05301, WO 90/11511, and WO 92/14138. For direct detection the labeling group can be selected from any known detectable marker groups, such as dyes, luminescent label-ing groups such as chemiluminescent groups, e.g. acri-dinium esters or dioxetanes, or fluorescent dyes, e.g. fluo-rescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay, e.g. EP-A-0 061 888), and radioisotopes.

Indirect detection systems comprise, for example, that the detection reagent, e.g., the detection antibody is labeled with a first partner of a binding pair. Examples of suitable binding pairs are antigen/antibody, biotin or biotin analogues such as aminobiotin, iminobiotin or desthiobiotin/avidin or Strepta-vidin, sugar/lectin, nucleic acid or nucleic acid analogue/complementary nucleic acid, and receptor/ligand, e.g., ste-roid hormone receptor/steroid hormone. In one preferred embodiment the first binding pair members comprise hap-ten, antigen and hormone. In one preferred embodiment the hapten is selected from the group consisting of digoxin, digoxygenin and biotin and analogues thereof. The second partner of such binding pair, e.g. an antibody, Streptavidin, etc., usually is labeled to allow for direct detection, e.g., by the labels as mentioned above.

Immunoassays can be performed generally in three dif-ferent formats. One is with direct detection, one with indi-rect detection, or by a sandwich assay. The direct detection immunoassay uses a detection (or tracer) antibody that can be measured directly. An enzyme or other molecule allows for the generation of a signal that will produce a color, fluorescence, or luminescence that allow for the signal to be visualized or measured (radioisotopes can also be used, although it is not commonly used today). In an indirect assay a primary antibody that binds to the analyte is used to provide a defined target for a secondary antibody (tracer antibody) that specifically binds to the target provided by the primary antibody (referred to as detector or tracer antibody). The secondary antibody generates the measurable signal. The sandwich assay makes use of two antibodies, a capture and a tracer (detector) antibody. The capture antibody is used to bind (immobilize) analyte from solution or bind to it in solution. This allows the analyte to be specifically removed from the sample. The tracer (detector) antibody is used in a second step to generate a signal (either directly or indirectly as described above). The sandwich format requires two antibodies each with a distinct epitope on the target molecule. In addition, they must not interfere with one another as both antibodies must be bound to the target at the same time.

Different principles for the determination of bispecific antibodies in an immunoassay are known to a person skilled in the art:
1) capture using
   one of the antigens;
   an anti-idiotypic antibody against one of the binding sites;
2) detection using
   the respective other antigen;
   an anti-idiotypic antibody against the respective other binding site;
These can be combined independently of each other.

Aspects of the Replacement Immunoassay According to the Invention

The invention is based, at least in part, on the finding that the determination of a multispecific, therapeutic antibody in as serum sample can be hampered by interference from monospecific antibodies comprising one binding specificity of the therapeutic antibody. These may be present due to the application of said monospecific antibody prior to the appli-cation of the multispecific, therapeutic antibody.

Normally, in an immunoassay for the determination of a multispecific, therapeutic antibody in a serum containing sample in a first step extraction of the therapeutic antibody from the sample is effected by a capture reagent bound to a solid phase that is specific for the multispecific, therapeutic antibody, such as, for example that is specifically binding to a binding specificity of the multispecific, therapeutic anti-body. In a second step the determination of the solid-phase-captured multispecific, therapeutic antibody is effected by a detection reagent, e.g. specifically binding to a binding specificity of the multispecific, therapeutic antibody differ-ent than that used in the capturing step. In FIG. 1 this is exemplified with anti-idiotypic antibodies for the first and second binding specificity of a bispecific, therapeutic anti-body as exemplary capture and detection reagents.

If the sample comprises besides the multispecific, thera-peutic antibody also a monospecific antibody that has at least one binding site with similar binding specificity as one of the therapeutic antibody's binding sites interference therefrom can occur by (non-specific) binding to the solid phase and thereby generation of a false positive signal, i.e. biasing the specificity of the assay based on the specificity of the capture reagent. This is depicted in FIG. 2. This is especially imminent if the monospecific antibody is present in excess of the multispecific antibody, e.g. in one embodi-ment 1,000-fold or more, in one embodiment 10,000-fold or more, or in one embodiment 100,000-fold or more.

It has now been found that such a non-specific biasing by a monospecific antibody can be reduced or even eliminated if the formed capture antibody-therapeutic antibody com-plex is desorbed from the solid phase by incubation with a replacement antibody that replaces the capture antibody in the immobilized complex. The thereby generated replace-ment antibody-therapeutic antibody complex is soluble and can be specifically detected after transfer to a new compart-ment. The capture of the desorbed complex for detection is preferably via a second binding specificity of the therapeutic antibody, thereby inverting the bridging assay. The non-specifically bound monospecific antibody is not desorbed in this step. Thereby the interference of the monospecific antibody can be reduced or even eliminated.

In one preferred embodiment, herein is reported a method for the determination of a multispecific, therapeutic anti-body, preferably a bispecific antibody, in a serum-containing sample comprising the following steps:
   a) incubating a solid phase to which a capture agent that is specifically binding to the therapeutic antibody has been immobilized with the sample to form an immo-bilized capture agent-therapeutic antibody-complex,
   b) incubating the solid phase with a replacement agent that competes with the capture agent for binding to the therapeutic antibody and thereby detaching the thera-peutic antibody from the solid phase by forming a solution comprising a replacement agent-therapeutic antibody-complex,
   c) determining in the solution obtained in step b) the replacement agent-therapeutic antibody-complex and thereby determining the therapeutic antibody in a serum-containing sample.

The capture agent and the replacement agent can be any compound that is specifically binding to the therapeutic antibody as long as both agents compete with each other for the binding site at the therapeutic antibody, i.e. as long as the replacement agent displaces the capture agent upon binding to the therapeutic antibody. Secondary parameters that influ-ence the efficiency of the replacement but not the taking place of the replacement as such are the used amount/excess of the replacement antibody and the incubation time.

Exemplary combinations or capture agent and replace-ment agent are:

capture agent: anti-idiotypic antibody 1; replacement agent: anti-idiotypic antibody 2; anti-idiotypic antibody 1 and 2 compete with each other for binding to the therapeutic antibody;

capture agent: one antigen of the therapeutic antibody; replacement agent: anti-idiotypic antibody; anti-idiotypic antibody competes with antigen for binding to the therapeutic antibody;

capture agent: anti-idiotypic antibody; replacement agent: antigen; anti-idiotypic antibody competes with antigen for binding to the therapeutic antibody;

capture agent: antigen; replacement agent: antigen capture agent: anti-mutant Fc-region antibody (e.g. anti-P329G antibody or anti-L234A/L235A antibody); replacement agent: anti-mutant Fc-region antibody (e.g. the same anti-PG antibody or the same anti-L234A/L235A antibody, respectively).

In one preferred embodiment, herein is reported a method for the determination of a multispecific, therapeutic antibody, preferably a bispecific antibody, in a serum-containing sample comprising the following steps:

a) incubating a solid phase to which a capture antibody that is specifically binding to the therapeutic antibody has been immobilized with the sample to form an immobilized capture antibody-therapeutic antibody-complex, b) incubating the solid phase with a replacement antibody that competes with the capture antibody for binding to the therapeutic antibody and thereby detaching the therapeutic antibody from the solid phase by forming a solution comprising a replacement antibody-therapeutic antibody-complex, c) determining in the solution obtained in step b) the replacement antibody-therapeutic antibody-complex and thereby determining the therapeutic antibody in a serum-containing sample.

The method according to the invention is in the following exemplified with an anti-CD3/CD20 bispecific antibody in the TCB format (CD20-TCB). This example is presented solely as an exemplification of the method according to the invention and shall not be construed as limitation. The true scope of the invention is set forth in the appended claims.

CD20-TCB and Gazyva®/Gazyvaro® (an anti-CD20 antibody) pretreatment represent a potent and safer approach for treatment of lymphoma patients and are currently being evaluated in phase I, multicenter study in patients with relapsed/refractory non-Hodgkin lymphoma (NCT03075696) (see Bacac, M., et al., Clin. Cancer. Res. 24 (2018) 1-13).

When using a standard state of the art bridging immunoassay according to the scheme depicted in FIG. 1 employing an anti-idiotypic anti-CD3 binding site antibody as capture antibody and an anti-idiotypic anti-CD20 binding site antibody as detection antibody for the determination of a bispecific CD20-TCB (concentration 1 ng/mL) in the presence of the respective monospecific anti-CD20 antibody (concentration 200 µg/mL) only a shallow curve can be obtained (see Example 1a, FIG. 3).

In the absence of the monospecific anti-CD20 antibody a steep curve is obtained (see Example 1b, FIG. 4).

The specific bridging immunoassay using an anti-idiotypic anti-CD3 binding site antibody for capturing the analyte was performed in the absence of the CD20-TCB with samples comprising only the monospecific anti-CD20 antibody. In this case a signal could be obtained in the presence as well as in the absence of the anti-idiotypic anti-CD3 binding site antibody (see Example 1c).

Thus, the interference of the monospecific anti-CD20 antibody in the CD20-TCB bridging assay stems from a non-specific interaction with the solid phase.

The CD20-TCB comprises a specific mutation in the Fc-region (P329G, numbering according to Kabat). Thus, an alternative bridging assay using an anti-P329G-Fc-region antibody as detection antibody was conducted. Therein a correct bridging signal was obtained in the presence as well as in the absence of the corresponding anti-CD20 antibody. But when using this assay setup information about the target-binding competence of the CD20 binding site of the CD20-TCB cannot be obtained as this binding site no longer contributes to the generated signal (see Example 2, FIG. 5).

Different approaches known from the art were tested to address the non-specific binding of the anti-CD20 antibody so that the target-binding competence of both binding sites of the CD20-TCB could be addressed in a single assay.

A simple switch of the capture and detection antibody is not feasible as an immobilized anti-idiotypic anti-CD20 binding site antibody will be saturated by the monospecific anti-CD20 antibody present in the sample and thereby the assay sensitivity will be greatly reduced.

Next a reduction of the streptavidin density used for the immobilization of the capture antibody on the solid phase was tested. Thereby the non-specific binding could be reduced but still the accuracy of the low quality control (LQC) and the lower limit of quantification quality control (LLQC) was affected (see Example 3). This effect was also not robust, so that, e.g., high inter-assay variations occurred resulting in a not suitable immunoassay (see Example 3).

Different buffers were tested. Use of 1% casein in PBS in combination with medium density streptavidin solid phase provided for a lower interference of the monospecific anti-CD20 antibody compared to the assay conducted in Universal Buffer. A suitable assay range was determined and assay performance was evaluated by accuracy assessment and inter assay precision of quality controls (QCs). Results showed a reduced interference but at the same time QCs and interference reduction were not robust showing a high inter-assay variation (see Example 4). Specificity/Selectivity assessment at LLQC level also revealed that the method was not robust enough as validation criterions regarding accuracy were not achieved (data not shown). Likewise using medium streptavidin density, Universal Buffer, and acidic washing conditions (pH 5.5) resulted in reduced interference but at the same time QCs and interference reduction were not robust showing a high inter-assay variation (see Example 5).

It has now been found that the above described problem is solved by including an intermediate replacement/displacement step in the method. That is, at first the CD20-TCB is captured by an anti-idiotypic anti-CD3 binding site antibody and thereafter the formed complex is displaced from the solid surface for analysis. In more detail, the capture of the CD20-TCB from the sample is achieved by incubation with an immobilized anti-idiotypic anti-CD3 binding site antibody on a first assay plate. After reaching equilibrium or after a specified time replacement of the immobilized capture antibody in the complex with soluble anti-idiotypic anti-CD3 binding site antibody (same as capture antibody or different, e.g. binding to the same epitope or sterically interfering, as long as the displacement can be effected) is effected. Thereby, without being bound by this theory, only bound CD20-TCB is set free into the supernatant, whereas non-specifically bound monospecific anti-CD20 antibody remains bound to the solid phase. Thereafter, the supernatant is transferred to a second assay plate on which an anti-idiotypic anti-CD20 binding site antibody is immobilized as capture antibody, i.e. inverting the bridging.

Thus, when using an immunoassay setup according to the invention the requirements of an assay sensitivity of 1 ng/mL or less and the identification of target binding competent CD20-TCB in the presence of a large excess (about 1:250,000) of monospecific anti-CD20 antibody are achieved. Additionally, the immunoassay according to the invention is feasible to be carried out within one working day and is robust.

Additionally, the immunoassay setup according to the invention can be carried out with a matrix content of up to 50% serum, allowing to increase sensitivity.

FIG. 6 shows the concentration-response curve for a bridging immunoassay according to the current invention comprising a displacement step. A good response can be obtained in the presence as well as in the absence of the respective monospecific anti-CD20 antibody. Example 6 recites the respective description and data.

The following Table provides a comparison of different assay formats and their characteristic properties as described above (ID=idiotypic).

| | conventional bridging assay with two anti-idiotypic antibodies | conventional bridging assay with one anti-idiotypic antibody and one anti-P329G antibody | bridging assay according to the current invention |
|---|---|---|---|
| capture antibody | anti-ID CD3 | anti-ID CD3 | anti-ID CD3 (plate 1) anti-ID CD20 (plate 2) |
| displacement | no | no | yes |
| detection antibody | anti-ID CD20 | anti-P329G | anti-ID CD3 |
| serum content | 10% (v/v) | 10% (v/v) | 50% (v/v) |
| assay range (ULQ-LLOQ) (serum conc.) | 100-1 ng/ml | 100-1 ng/ml | 40-0.63 ng/ml |
| interference | yes | no | no |
| target-binding competence | yes for both | only for capture specificity | yes for both |

The assay according to the current invention for the CD20-TCB was successfully qualified.

| intra-assay variations | n | accuracy mean, %] | precision [CV, %] |
|---|---|---|---|
| LLQC nominal 0.625 ng/ml | 4 | 111 | 6.8 |
| LQC nominal 1.875 ng/ml | 4 | 109 | 5.5 |
| MQC nominal 7.5 ng/ml | 5 | 104 | 2.8 |
| HQC nominal 30 ng/ml | 5 | 103 | 1.9 |
| ULQC nominal 40 ng/mL | 5 | 102 | 3.2 |
| LLQC nominal 0.625 ng/ml | 7 | 107 | 9.5 |
| LQC nominal 1.875 ng/ml | 7 | 103 | 8.3 |
| MQC nominal 7.5 ng/ml | 7 | 103 | 4.4 |
| HQC nominal 30 ng/ml | 7 | 99 | 2.8 |
| ULQC nominal 40 ng/ml | 7 | 98 | 2.6 |

The following examples and figures are provided to aid the understanding of the present invention, the true scope of which is set forth in the appended claims. It is understood that modifications can be made in the procedures set forth without departing from the spirit of the invention.

EXAMPLE 1

Bridging Immunoassay with Double Anti-Idiotypic Antibody

Figure 1:
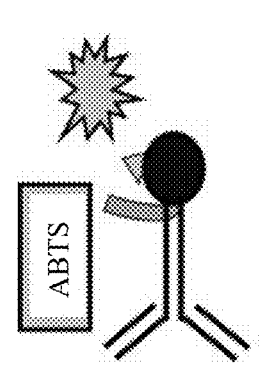
FIG. 1 Scheme of an immunoassay for the determination of a bispecific antibody: immobilization of the bispecific antibody to the solid phase (SA-MTP; streptavidin-coated micro titer plate) by a capture reagent and determination of the bound bispecific antibody by detection reagent.
Figure 1:
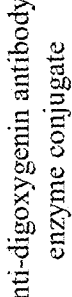
Figure 1:
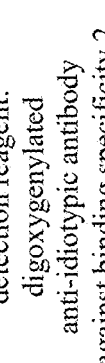
Figure 1:
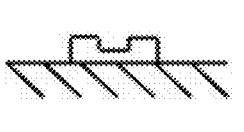
Figure 1:
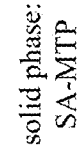
Figure 2:
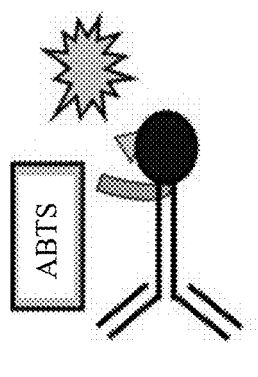
FIG. 2 Scheme of biased immunoassay: direct interaction of the monospecific antibody with the solid phase and thereby biasing the specific capture step.
Figure 2:
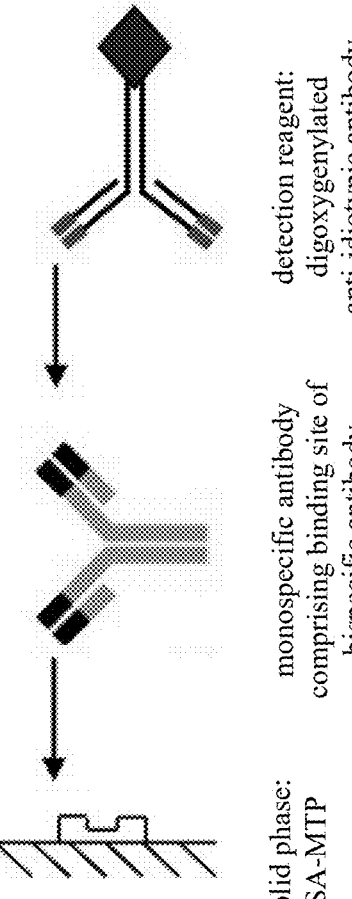
Figure 3:
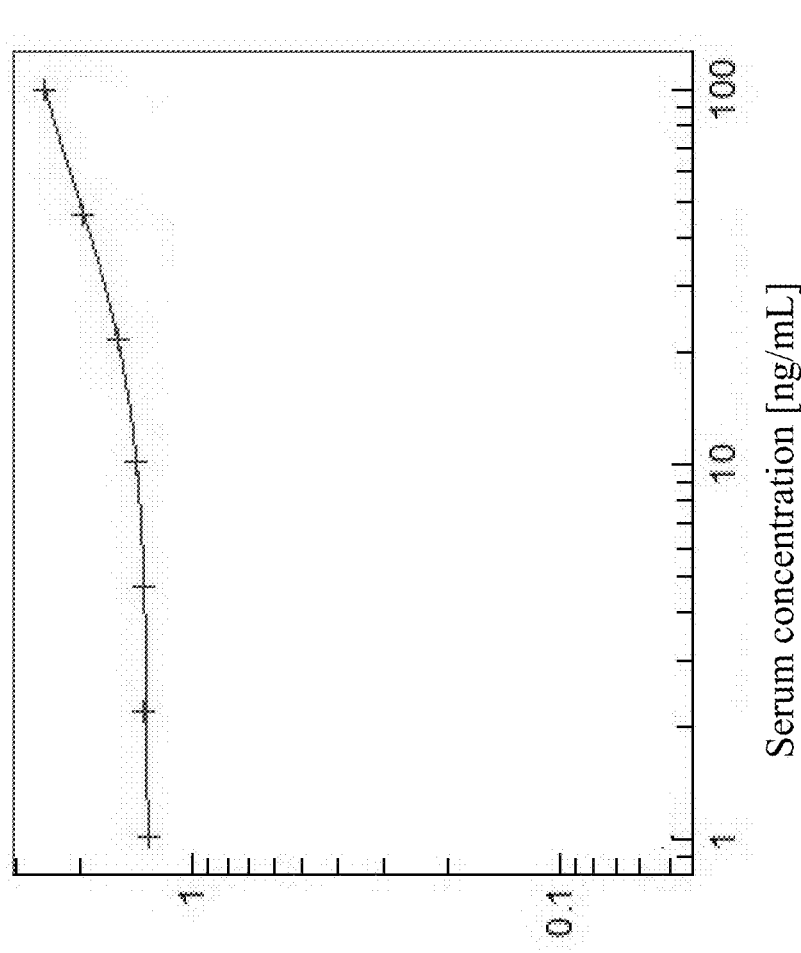
FIG. 3 Concentration-response curve for a bridging immunoassay employing an anti-idiotypic anti-CD3 binding site antibody as capture antibody and an anti-idiotypic anti-CD20 binding site antibody as detection antibody for the determination of a bispecific CD20-TCB in the presence of the respective monospecific anti-CD20 antibody.
Figure 4:
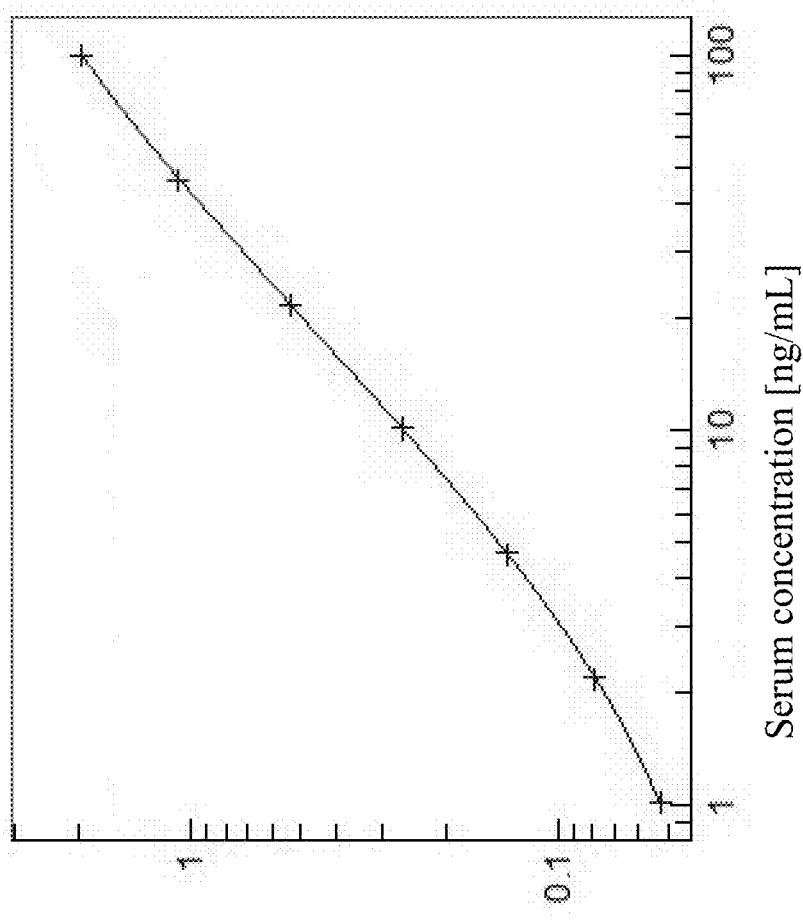
FIG. 4 Concentration-response curve for a bridging immunoassay employing an anti-idiotypic anti-CD3 binding site antibody as capture antibody and an anti-idiotypic anti-CD20 binding site antibody as detection antibody for the determination of a bispecific CD20-TCB in the absence of the respective monospecific anti-CD20 antibody.
Figure 5:
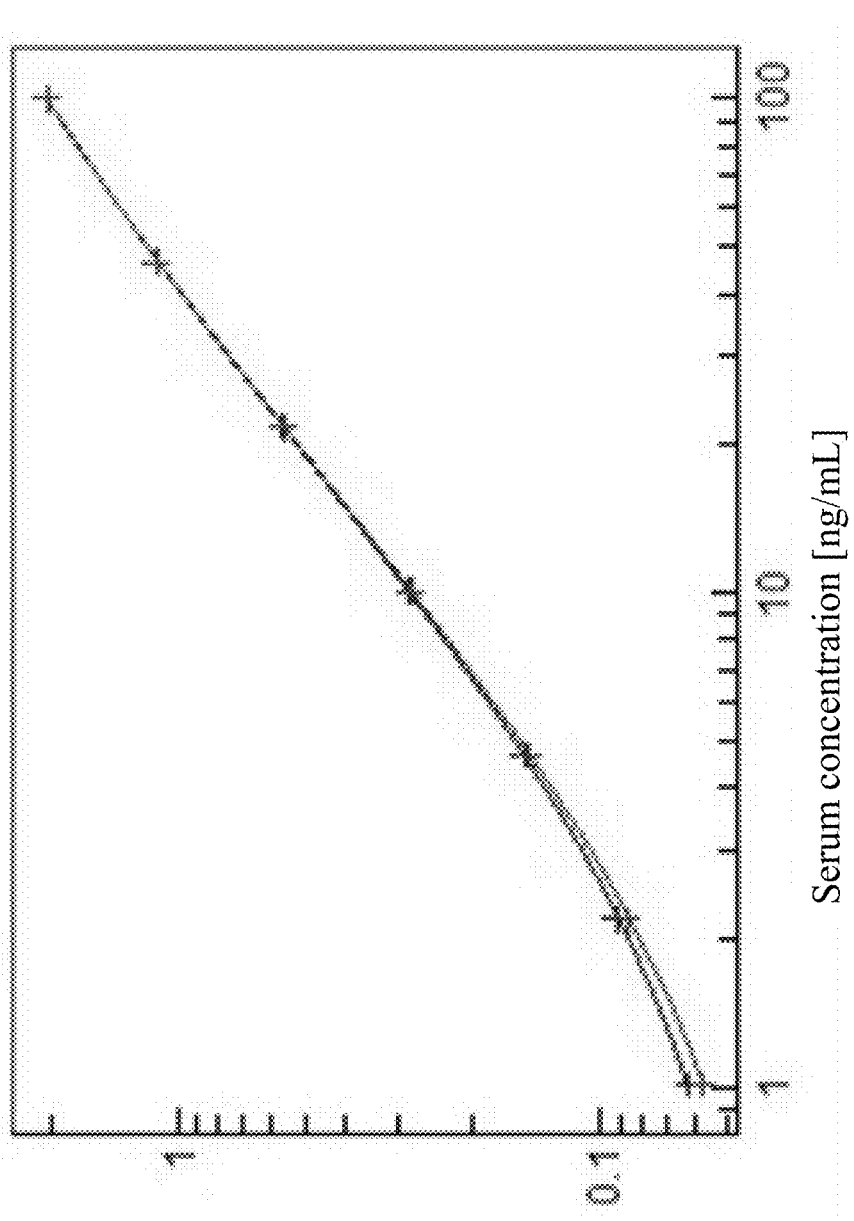
FIG. 5 Concentration-response curve for a bridging immunoassay employing an anti-idiotypic anti-CD3 binding site antibody as capture antibody and an anti-P329G antibody as detection antibody for the determination of a bispecific CD20-TCB in the presence and absence of the respective monospecific anti-CD20 antibody.
Figure 6:
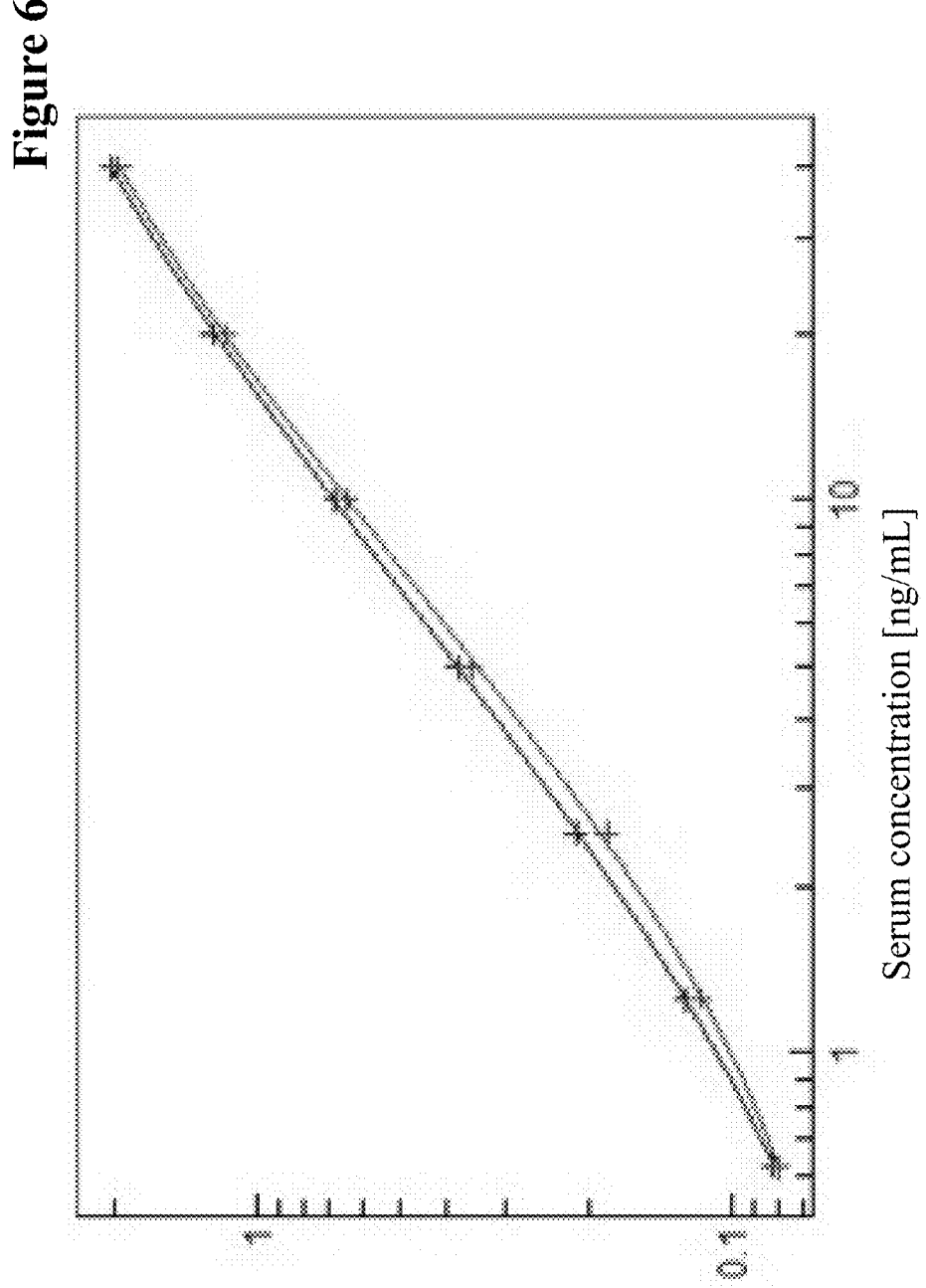
FIG. 6 Concentration-response curve for a bridging immunoassay according to the current invention comprising an additional displacement step in the presence as well as in the absence of the respective monospecific anti-CD20 antibody.

General Procedure:

Murine monoclonal antibodies were produced by Roche Diagnostics GmbH (Germany). As anti-idiotypic anti-CD3 binding site antibody biotinylated M-4.25.93-IgG was used and as anti-idiotypic anti-CD20 binding site antibody digoxigenylated M-6.15.528-IgG-Dig was used.

CD20-TCB calibrators or QCs (quality controls) as well as samples with CD20-TCB and anti-CD20 antibody were prepared in 100% pooled human serum obtained from Trina Bioreactives, Switzerland or 100% Cynomolgus pooled serum (Seralab, UK).

Antibody preparations and serum sample dilutions were made in Universal Buffer (Roche Diagnostics GmbH, Germany). Each washing included 3 steps with 300 µL PBS, 0.05% Tween 20 (Sigma Aldrich, Germany), incubation steps were carried out at room temperature with shaking at 500 rpm and the working volume per well was 100 µL.

For capturing Streptavidin plates (high binding capacity, Microcoat GmbH, Bernried, Germany) were coated with 0.2 µg/mL M-4.25.93-IgG-Bi for one hour and unbound antibody was removed by washing followed by addition of diluted (1:10) serum samples and incubation for one hour. After washing analyte detection was performed by successive addition of M-6.15.528-IgG-Dig (0.2 µg/mL, 50 min) and <Dig>-Fab fragments covalently bound to horseradish peroxidase (Roche Diagnostics GmbH, Germany; 40 mU, 50 min). A washing step was applied in between and after this step. ABTS (2'2'-azino-bis-3-ethyl-benzthiazoline-6-sulphonic acid; Roche Diagnostics GmbH, Germany) was added as substrate for color reaction, which was monitored by photometrical read-out at 405 nm (reference wavelength 490 nm). Samples were analyzed in duplicates and mean absorbance values were calculated and further processed. Concentrations were determined by back calculation from the calibration curve with a non-linear 4-parameter curve-fitting function (Wiemer-Rodbard). Accuracy was calculated in relation to nominal concentrations in the spiked serum samples.

| a) Sample comprising CD20-TCB and 200 μg/mL anti-CD20 antibody: | | |
|---|---|---|
| nominal concentration [ng/mL] | measured concentration [ng/ml] | accuracy [%] |
| ULQC | 100.00 | 142.47 | 142 |
| HQC | 75.00 | 125.36 | 167 |
| MQC | 15.00 | 69.10 | 461 |
| LQC | 3.00 | 61.12 | 2037 |
| LLQC | 1.00 | 59.00 | 5900 |
| blank | 0 | 56.92 | — |

| b) Sample comprising CD20-TCB only: | | |
|---|---|---|
| nominal concentration [ng/ml] | measured concentration [ng/ml] | accuracy [%] |
| ULQC | 100.00 | 104.95 | 105 |
| HQC | 75.00 | 80.83 | 108 |
| MQC | 15.00 | 15.58 | 104 |
| LQC | 3.00 | 3.42 | 114 |
| LLQC | 1.00 | 1.07 | 107 |
| blank | 0 | b.l.q. | — |

| c) Sample comprising anti-CD20 antibody only (values back calculated on a CD20-TCB Calibration curve in 10% cynomolgus monkey serum): | | |
|---|---|---|
| | measured concentration [ng/ml] | |
| nominal concentration [μg/mL] | solid phase coated with anti-idiotypic anti-CD3 binding site antibody | solid phase without anti-idiotypic anti-CD3 binding site antibody |
| 500.00 | 47.97 | 52.30 |
| 50.00 | 23.84 | 26.59 |
| 5.00 | 7.26 | 7.40 |
| 0 | b.l.q. | b.l.q. |

EXAMPLE 2

Bridging Immunoassay with Anti-Idiotypic Antibody Capture and Anti-P329G Antibody Detection General Procedure:

General: 4 Step Sandwich Elisa

Incubation at room temperature with shaking at 500 rpm
Working value: 100 μL
Washing (denoted as w hereafter): 3×300 μL PBS, 0.05% Tween 20
Replicates n=2, calculation of mean absorbance value
Calibration curve fit: non-linear 4-parameter curve-fitting function (Wiemer-Rodbard)
Assay range: 1 ng/mL-100 ng/mL Reagents:

Human pooled serum; Trina Bioreactives, Switzerland
Murine monoclonal antibodies; Roche Diagnostics GmbH, Germany Anti-idiotypic anti-CD3 binding site antibody, bioti-nylated: M-4.25.93-IgG-Bi
Anti-P329G antibody, digoxigenylated: M-1.7.24-IgG-Dig
Streptavidin plate (high binding capacity); Microcoat GmbH, Bernried, Germany
Universal Buffer (denoted as UB hereinafter); Roche Diagnostics GmbH, Germany
Washing buffer; 1×PBS, 0.05% Tween (Sigma Aldrich, Germany)
<Dig>-Fab fragments covalently bound to horseradish peroxidase (<Dig>-Fab-POD); Roche Diagnostics GmbH, Germany
2'2'-azino-bis-3-ethyl-benzthiazoline-6-sulphonic acid (ABTS); Roche Diagnostics GmbH, Germany Assay conduct:

Coating: 0.2 μg/mL M-4.25.93-IgG-Bi, 1 hour, w
Sample: 1 to 10 in UB, 1 hour, w
Detection 1: 0.2 μg/mL M-1.7.24-IgG-Dig, 50 min, w
Detection 2: 50 mU <Dig>-Fab-POD, 50 min, w
Substrate reaction: ABTS, repeated absorbance measurement at 405 nm (reference wavelength 490 nm)

| a) Sample comprising CD20-TCB and 200 μg/mL anti-CD20 antibody: | | |
|---|---|---|
| nominal concentration [ng/ml] | measured concentration [ng/ml] | accuracy [%] |
| ULQC | 100.00 | 95.41 | 95 |
| HQC | 75.00 | 72.48 | 97 |
| MQC | 15.00 | 13.17 | 88 |
| LQC | 3.00 | 3.09 | 103 |
| LLQC | 1.00 | 1.07 | 107 |
| blank | 0 | b.l.q. | — |

| b) Sample comprising CD20-TCB only: | | |
|---|---|---|
| nominal concentration [ng/ml] | measured concentration [ng/ml] | accuracy [%] |
| ULQC | 100.00 | 96.40 | 96 |
| HQC | 75.00 | 73.77 | 98 |
| MQC | 15.00 | 13.33 | 89 |
| LQC | 3.00 | 3.14 | 105 |
| LLQC | 1.00 | 1.14 | 114 |
| blank | 0 | b.l.q. | — |

EXAMPLE 3

Bridging Immunoassay with Double Anti-Idiotypic Antibody at Reduced Immobilization Densities General Procedure:

Same procedure as described in Example 1, except for use of Streptavidin plate with medium binding capacity, Microcoat GmbH, Bernried, Germany a) Sample comprising CD20-TCB and 200 µg/mL anti-CD20 antibody:

| | nominal concentration [ng/ml] | measured concentration [ng/ml] | accuracy [%] |
|---|---|---|---|
| ULQC | 100.00 | 102.01 | 102 |
| HQC | 75.00 | 78.84 | 105 |
| MQC | 15.00 | 16.59 | 111 |
| LQC | 3.00 | 4.48 | 149 |
| LLQC | 1.00 | 2.41 | 241 |
| blank | 0 | 1.27 | — | b) Sample comprising CD20-TCB only:

| | nominal concentration [ng/ml] | measured concentration [ng/ml] | accuracy [%] |
|---|---|---|---|
| ULQC | 100.00 | 101.17 | 101 |
| HQC | 75.00 | 78.43 | 105 |
| MQC | 15.00 | 15.67 | 104 |
| LQC | 3.00 | 3.33 | 111 |
| LLQC | 1.00 | 1.05 | 105 |
| blank | 0 | b.l.q. | — |

EXAMPLE 4

Bridging Immunoassay with Double Anti-Idiotypic Antibody at Reduced Immobilization Densities with 1% Casein in PBS as Assay Buffer General Procedure:

General: 4 Step Sandwich ELISA

Incubation at room temperature with shaking at 500 rpm

Working value: 100 µL

Washing (denoted as w hereinafter): 3×300 µL PBS, 0.05% Tween 20

Replicates n=2, calculation of mean absorbance value

Calibration curve fit: non-linear 4-parameter curve-fitting function (Wiemer-Rodbard)

Assay range: 1 ng/mL-64 ng/mL

Reagents:

Human pooled serum; Trina Bioreactives, Switzerland

Murine monoclonal antibodies; Roche Diagnostics GmbH, Germany

Anti-idiotypic anti-CD3 binding site antibody, biotinylated: M-4.25.93-IgG-Bi

Anti-idiotypic anti-CD20 binding site antibody, digoxigenylated: M-6.15.528-IgG-Dig Streptavidin plate (medium binding capacity); Microcoat GmbH, Bernried, Germany Casein (Hammersten); VWR Prolabo Chemicals, Germany Assay buffer (denoted as AB hereinafter): 1% Casein in 1×PBS (Roche Diagnostics GmbH, Germany)

Washing buffer; 1×PBS, 0.05% Tween (Sigma Aldrich, Germany)

<Dig>-Fab fragments covalently bound to horseradish peroxidase (<Dig>-Fab-POD); Roche Diagnostics GmbH, Germany 2'2'-azino-bis-3-ethyl-benzthiazoline-6-sulphonic acid (ABTS); Roche Diagnostics GmbH, Germany Assay Conduct:

Coating: 0.25 µg/mL M-4.25.93-IgG-Bi, 1 hour, w

Sample: 1 to 10 in AB, 1 hour, w

Detection 1: 0.25 µg/mL M-6.15.528-IgG-Dig, 60 min, w

Detection 2: 40 mU <Dig>-Fab-POD, 60 min, w

Substrate reaction: ABTS, repeated absorbance measurement at 405 nm (reference wavelength 490 nm)

a) Sample comprising CD20-TCB and 200 µg/mL anti-CD20 antibody:

| | nominal conc. [ng/mL] | measured conc. 1 [ng/mL] | measured conc. 2 [ng/mL] | measured conc. 3 [ng/mL] | measured conc. 4 [ng/mL] | precision [%] |
|---|---|---|---|---|---|---|
| ULQC | 64.00 | 66.40 | 80.55 | 52.93 | 43.76 | 26 |
| HQC | 48.00 | 52.90 | 59.85 | 39.51 | 34.73 | 25 |
| MQC | 12.00 | 12.29 | 13.13 | 8.17 | 7.58 | 27 |
| LQC | 3.00 | 3.72 | 3.85 | 2.31 | 2.34 | 28 |
| LLQC | 1.00 | 1.39 | 1.60 | 0.99 | 1.07 | 23 |

| | nominal conc. [ng/mL] | accuracy 1 [%] | accuracy 2 [%] | accuracy 3 [%] | accuracy 4 [%] | precision [%] |
|---|---|---|---|---|---|---|
| ULQC | 64.00 | 104 | 126 | 83 | 68 | 26 |
| HQC | 48.00 | 110 | 125 | 82 | 72 | 25 |
| MQC | 12.00 | 102 | 109 | 68 | 63 | 27 |
| LQC | 3.00 | 124 | 128 | 77 | 78 | 28 |
| LLQC | 1.00 | 139 | 160 | 99 | 107 | 23 |

| b) Sample comprising CD20-TCB only: | | | | | |
|---|---|---|---|---|---|
| | nominal conc. [ng/mL] | measured conc. 1 [ng/mL] | measured conc. 2 [ng/mL] | measured conc. 3 [ng/mL] | measured conc. 4 [ng/mL] | pre-cision [%] |

| | nominal conc. [ng/mL] | measured conc. 1 [ng/mL] | measured conc. 2 [ng/mL] | measured conc. 3 [ng/mL] | measured conc. 4 [ng/mL] | pre-cision [%] |
|---|---|---|---|---|---|---|
| ULQC | 64.00 | 57.53 | 61.02 | 56.93 | 49.57 | 9 |
| HQC | 48.00 | 45.43 | 51.75 | 47.17 | 44.61 | 7 |
| MQC | 12.00 | 10.46 | 11.98 | 8.07 | 10.05 | 16 |
| LQC | 3.00 | 3.03 | 3.11 | 2.10 | 2.65 | 17 |
| LLQC | 1.00 | 1.00 | 1.11 | 0.69 | 0.98 | 19 |

| | nominal conc. [ng/mL] | accuracy 1 [%] | accuracy 2 [%] | accuracy 3 [%] | accuracy 4 [%] | pre-cision [%] |
|---|---|---|---|---|---|---|
| ULQC | 64.00 | 90 | 95 | 89 | 77 | 9 |
| HQC | 48.00 | 95 | 108 | 98 | 93 | 7 |
| MQC | 12.00 | 87 | 100 | 67 | 84 | 16 |
| LQC | 3.00 | 101 | 104 | 70 | 88 | 17 |
| LLQC | 1.00 | 100 | 111 | 69 | 98 | 19 |

EXAMPLE 5

Bridging Immunoassay with Double Anti-Idiotypic Antibody at Reduced Immobilization Densities Under Acidic (pH 5.5) Washing Conditions General Procedure:
General: 4 Step Sandwich ELISA
Incubation at room temperature with shaking at 500 rpm
Working value: 100 µL
Washing (denoted as w hereinafter): 3×300 µL PBS, 0.05% Tween 20, pH 5.5
Replicates n=2, calculation of mean absorbance value
Calibration curve fit: non-linear 4-parameter curve-fitting function (Wiemer-Rodbard)
Assay range: 1 ng/mL-64 ng/mL Reagents:
Human pooled serum; Trina Bioreactives, Switzerland
Murine monoclonal antibodies; Roche Diagnostics GmbH, Germany
Anti-idiotypic anti-CD3 binding site antibody, biotinylated: M-4.25.93-IgG-Bi
Anti-idiotypic anti-CD20 binding site antibody, digoxigenylated: M-6.15.528-IgG-Dig Streptavidin plate (medium binding capacity); Microcoat GmbH, Bernried, Germany
Assay buffer: Universal Buffer (denoted UB hereinafter); Roche Diagnostics GmbH, Germany
Washing buffer; 1×PBS, 0.05% Tween, pH 5.5 (Sigma Aldrich, Germany, pH adjusted with 2 M HCl, Sigma Aldrich, Germany)
<Dig>-Fab fragments covalently bound to horseradish peroxidase (<Dig>-Fab-POD); Roche Diagnostics GmbH, Germany
3,3',5,5'-Tetramethyl benzidine (TMB); Roche Diagnostics GmbH, Germany
1 M $H_2SO_4$; Carl Roth, Germany Assay Conduct:
Coating: 0.25 µg/mL M-4.25.93-IgG-Bi, 1 hour, w
Sample: 1 to 10 in UB, 1 hour, w
Detection 1: 0.25 µg/mL M-6.15.528-IgG-Dig, 60 min, w
Detection 2: 10 mU <Dig>-Fab-POD, 60 min, w
Substrate reaction: TMB, stopped with 50 µL 1 M $H_2SO_4$
Photometrical read-out at 450 nm (reference wavelength 690 nm)

| a) Sample comprising CD20-TCB and 200 µg/mL anti-CD20 antibody: | | | | | |
|---|---|---|---|---|---|
| | nominal conc. [ng/mL] | measured conc. 1 [ng/mL] | measured conc. 2 [ng/mL] | measured conc. 3 [ng/mL] | measured conc. 4 [ng/mL] | pre-cision [%] |

| | nominal conc. [ng/mL] | measured conc. 1 [ng/mL] | measured conc. 2 [ng/mL] | measured conc. 3 [ng/mL] | measured conc. 4 [ng/mL] | pre-cision [%] |
|---|---|---|---|---|---|---|
| ULQC | 64.00 | 55.54 | 35.06 | 58.56 | 56.44 | 21 |
| HQC | 48.00 | 42.89 | 30.55 | 44.88 | 47.12 | 18 |
| MQC | 12.00 | 10.10 | 6.74 | 9.80 | 11.95 | 22 |
| LQC | 3.00 | 2.74 | 1.85 | 2.57 | 3.24 | 22 |
| LLQC | 1.00 | 1.05 | 0.81 | 1.09 | 1.70 | 33 |

| | nominal conc. [ng/mL] | accuracy 1 [%] | accuracy 2 [%] | accuracy 3 [%] | accuracy 4 [%] | pre-cision [%] |
|---|---|---|---|---|---|---|
| ULQC | 64.00 | 87 | 55 | 91 | 88 | 21 |
| HQC | 48.00 | 89 | 64 | 94 | 98 | 18 |
| MQC | 12.00 | 84 | 56 | 82 | 100 | 22 |
| LQC | 3.00 | 91 | 62 | 86 | 108 | 22 |
| LLQC | 1.00 | 105 | 81 | 109 | 170 | 33 |

| b) Sample comprising CD20-TCB only: | | | | | |
|---|---|---|---|---|---|
| | nominal conc. [ng/mL] | measured conc. 1 [ng/mL] | measured conc. 2 [ng/mL] | measured conc. 3 [ng/mL] | measured conc. 4 [ng/mL] | pre-cision [%] |
| ULQC | 64.00 | 56.24 | 44.84 | 60.61 | 51.59 | 13 |
| HQC | 48.00 | 43.67 | 34.35 | 46.80 | 45.26 | 13 |
| MQC | 12.00 | 11.87 | 8.47 | 12.11 | 11.27 | 15 |
| LQC | 3.00 | 2.96 | 2.12 | 2.97 | 2.43 | 16 |
| LLQC | 1.00 | 0.98 | 0.85 | 1.34 | 1.03 | 20 |

| | nominal conc. [ng/mL] | accuracy 1 [%] | accuracy 2 [%] | accuracy 3 [%] | accuracy 4 [%] | pre-cision [%] |
|---|---|---|---|---|---|---|
| ULQC | 64.00 | 88 | 70 | 95 | 81 | 13 |
| HQC | 48.00 | 91 | 72 | 98 | 94 | 13 |
| MQC | 12.00 | 99 | 71 | 101 | 94 | 15 |
| LQC | 3.00 | 99 | 71 | 99 | 81 | 16 |
| LLQC | 1.00 | 98 | 85 | 134 | 103 | 20 |

EXAMPLE 6

Bridging Immunoassay According to the Current Invention

General Procedure:

Murine monoclonal antibodies were produced by Roche Diagnostics GmbH (Germany). As anti-idiotypic anti-CD3 binding site antibodies biotinylated M-4.35.77-IgG as well as digoxigenylated M-4.25.93-IgG were used and as anti-idiotypic anti-CD20 binding site antibody biotinylated M-6.15.528 was used.

CD20-TCB calibrators or QCs (quality controls) as well as samples with CD20-TCB and anti-CD20 antibody were prepared in 100% pooled human serum obtained from Trina Bioreactives, Switzerland. Antibody preparations and serum sample dilutions were made in Universal Buffer (Roche Diagnostics GmbH, Germany). Each washing included 3 steps with 300 µL PBS, 0.05% Tween 20 (Sigma Aldrich, Germany). Incubation steps were carried out at room temperature with shaking at 500 rpm. The procedure was divided into two parts conducted on two streptavidin coated microtiter plates (SA-MTP 1 and 2, high binding capacity, Microcoat GmbH, Bernried, Germany).

Part 1: For capturing SA-MTP 1 was coated with 135 µL/well of 0.21 µg/mL M-4.35.77-IgG-Bi for one hour and unbound antibody was removed by washing followed by successive addition of 67.5 µL/well Universal buffer and 67.5 µL/well serum sample (resulting in 50% Matrix) and incubation for 35 minutes. After washing 135 µL of 1 µg/mL M-4.25.93-Dig (detection antibody) was added and the plate was incubated for 2.5 hours without a following washing step for desorption (replacement step).

Part 2: 90 minutes after addition of detection antibody to SA-MTP1, SA-MTP2 was coated with 100 µL/well 0.25 µg/mL M-6.28.530-Bi for one hour followed by washing. Thereafter 100 µL of the formed complexes (drug-detection antibody) were transferred from SA-MTP1 to SA-MTP2 and incubated for 35 minutes. As second detection reagent 100 µL/well 50 mU <Dig>-Fab fragments covalently bound to horseradish peroxidase (Roche Diagnostics GmbH, Germany) was added and the plate was incubated for 45 Minutes. A washing step was applied before and after this step. 100 µL/well ABTS (2'2'-azino-bis-3-ethyl-benzthiazoline-6-sulphonic acid; Roche Diagnostics GmbH, Germany) was used as substrate for color reaction, which was monitored by photometrical read-out at 405 nm (reference wavelength 490 nm). Samples were analyzed in duplicates and mean absorbance values were calculated and further processed. Concentrations were determined by back calculation from the calibration curve with a non-linear 4-parameter curve-fitting function (Wiemer-Rodbard). Accuracy was calculated in relation to nominal concentrations in the spiked serum samples.

| a) Sample comprising CD20-TCB and 200 µg/mL anti-CD20 antibody: | | | |
|---|---|---|---|
| | nominal concentration [ng/ml] | measured concentration ng/ml | accuracy [%] |
| ULQC | 40.00 | 41.31 | 103 |
| HQC | 30.00 | 30.58 | 102 |
| MQC | 7.50 | 7.13 | 95 |
| LQC | 1.88 | 1.72 | 92 |
| LLQC | 0.63 | 0.51 | 82 |
| blank | 0 | b.l.q. | — |

| b) Sample comprising CD20-TCB only: | | | |
|---|---|---|---|
| | nominal concentration [ng/ml] | measured concentration [ng/ml] | accuracy [%] |
| ULQC | 40.00 | 41.90 | 105 |
| HQC | 30.00 | 31.07 | 104 |
| MQC | 7.50 | 7.05 | 94 |
| LQC | 1.88 | 1.77 | 95 |
| LLQC | 0.63 | 0.54 | 86 |
| blank | 0 | b.l.q. | — |

The invention claimed is:

1. A method for the determination of a bispecific antibody in a serum-containing sample comprising the following steps:

a) incubating a solid phase with the serum-containing sample, wherein the serum-containing sample comprises the bispecific antibody and a monospecific antibody, wherein the bispecific antibody comprises a first binding site that binds to a first antigen and a second binding site that binds to a second antigen, and wherein the monospecific antibody comprises the second binding site, wherein the solid phase comprises a capture antibody immobilized thereon, wherein the capture antibody specifically binds the first binding site to form an immobilized capture antibody-bispecific antibody-complex, and wherein the mono-specific antibody nonspecifically binds the solid phase, b) optionally washing the solid phase whereby the capture antibody-bispecific antibody-complex remains bound to the solid phase, c) incubating the solid phase with a solution comprising a replacement antibody that competes with the capture antibody for binding to the first binding site of the bispecific antibody, thereby forming a replacement antibody-bispecific antibody-complex in the solution, wherein the monospecific antibody remains bound to the solid phase, and d) determining the replacement antibody-bispecific antibody-complex in the solution of step c) and thereby determining the bispecific antibody in a serum-containing sample.

2. The method according to claim 1, wherein the replacement antibody is labelled and the determining of the replacement antibody-bispecific antibody-complex is by detecting said label.

3. The method according to claim 1, wherein the replacement antibody is the capture antibody.

4. The method according to claim 1, wherein the solid phase in step c) is incubated with the replacement antibody at a concentration of 6.67 nM or more.

5. The method according to claim 1, wherein the bispecific antibody is an anti-CD3/CD20 bispecific antibody.

6. The method according to claim 5, wherein the bispecific anti-CD3/CD20 antibody is RG6026.

7. The method according to claim 1, wherein the monospecific antibody is an anti-CD20 antibody.

8. The method according to claim 7, wherein the anti-CD20 antibody is obinutuzumab.

9. The method according to claim 1, wherein the determining in step d) comprises (i) transferring the solution comprising the soluble replacement antibody-bispecific antibody-complex to a second solid phase comprising a second capture antibody, wherein the second capture antibody specifically binds to the second antigen binding site of the bispecific antibody, to form an immobilized second capture antibody-bispecific antibody-complex, and (ii) detecting the immobilized second capture antibody-bispecific antibody-complex.

* * * * *